United States Patent [19]

Collins

[11] 4,212,258
[45] Jul. 15, 1980

[54] UNDERWATER APPARATUS FOR ACOUSTICALLY INSPECTING A SUBMERGED OBJECT

[75] Inventor: H. Dale Collins, Richland, Wash.
[73] Assignee: International Submarine Services, S.A., London, England
[21] Appl. No.: 905,203
[22] Filed: May 12, 1978
[51] Int. Cl.² .............................................. B63G 8/00
[52] U.S. Cl. ..................................... 114/312; 73/603; 73/626; 367/8; 367/11; 367/105; 367/910; 405/185
[58] Field of Search ............ 114/312, 313; 340/5 MP, 340/3 R, 5 H; 405/185; 73/620, 626, 603

[56] References Cited

U.S. PATENT DOCUMENTS

| | | | |
|---|---|---|---|
| 3,045,206 | 7/1962 | Ahrens et al. | 340/3 R |
| 3,067,281 | 12/1962 | Pierre et al. | 178/6.8 |
| 3,500,648 | 3/1970 | Daniell | 114/313 X |
| 3,721,312 | 3/1973 | John | 181/0.5 R |
| 3,886,489 | 5/1975 | Jones | 340/5 MP |
| 3,979,711 | 9/1976 | Maginness | 340/5 MP |
| 4,021,771 | 3/1977 | Collins et al. | 340/5 H |
| 4,102,203 | 7/1978 | Sylvester et al. | 73/620 |
| 4,140,022 | 2/1979 | Maslak | 73/626 |

Primary Examiner—Sherman D. Basinger
Attorney, Agent, or Firm—Wells, St. John & Roberts

[57] ABSTRACT

An underwater apparatus is described for acoustically inspecting a submerged object at considerable depths such as the lower structural portion of an off-shore drilling rig to determine if the structure has internal defect which cannot be optically detected. The apparatus is intended to operate in depths of up to 500 meters. The apparatus includes an underwater craft for transporting both humans and equipment to the submerged object. The apparatus includes a hand held acoustical and optical probe that is movable by a diver over the surface of the submerged object. The probe includes an array of acoustical transducers that are sequentially activated to acoustically scan the interior of the object. The acoustical transducers are mounted in a flexible support material to accommodate the array to the contour of the surface. The probe additionally includes a real-time display of the acoustical information to assist the diver in effectively inspecting the object. Additionally the probe includes an optical system for visually inspecting the exterior of the surface being inspected.

7 Claims, 4 Drawing Figures

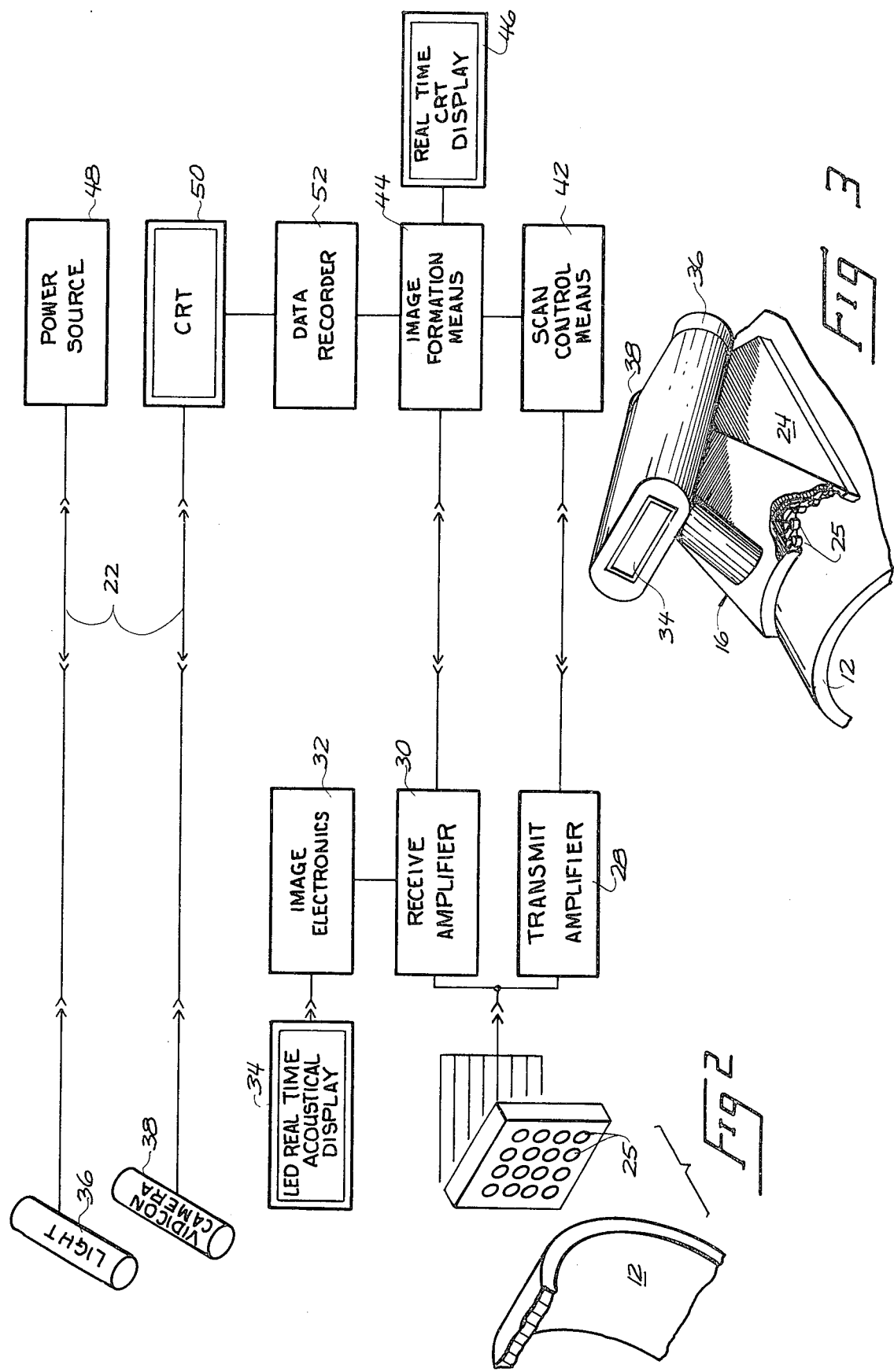

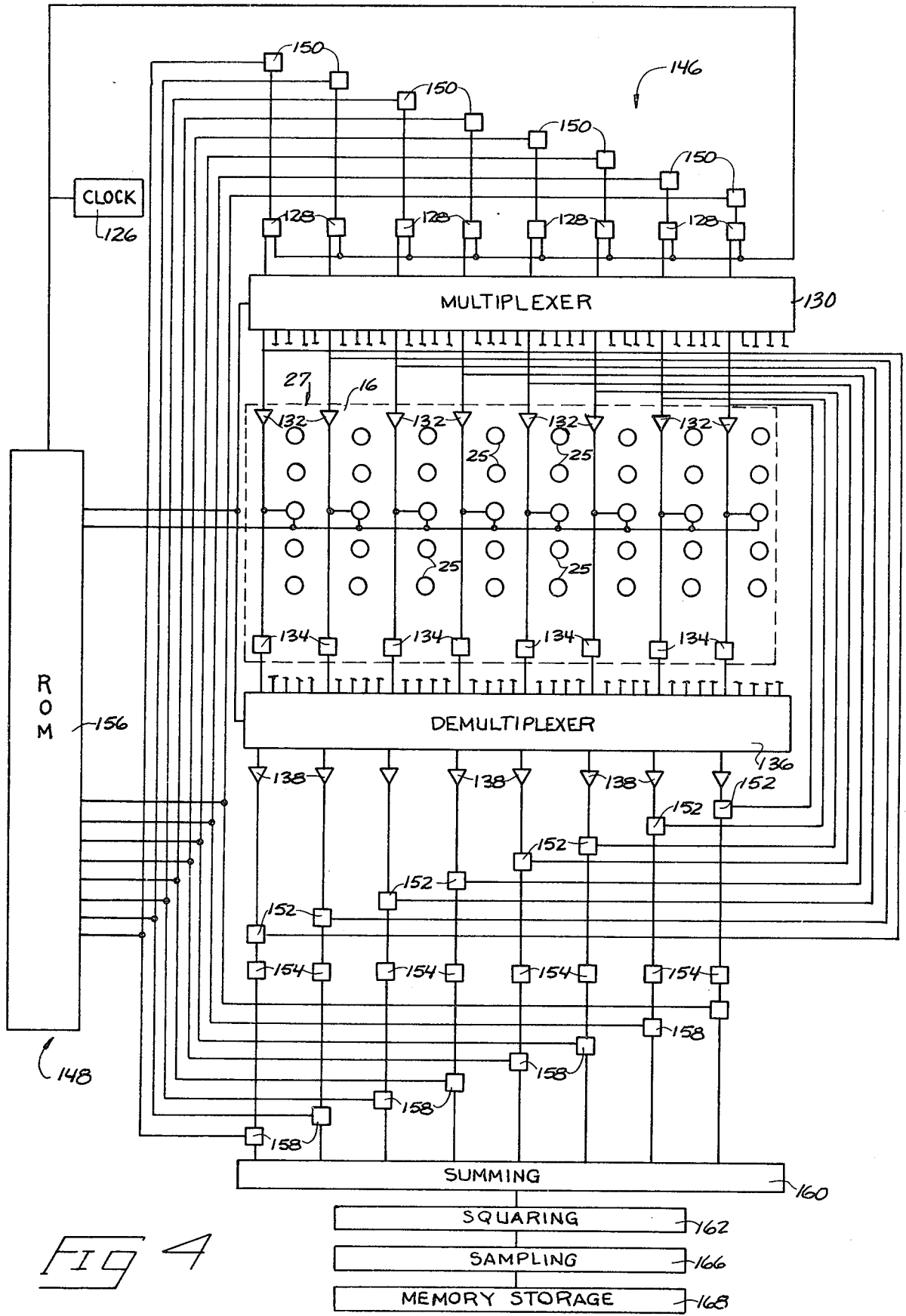

UNDERWATER APPARATUS FOR ACOUSTICALLY INSPECTING A SUBMERGED OBJECT

BACKGROUND OF THE INVENTION

This invention relates to underwater investigatory systems and more particularly to underwater apparatus for inspecting the interior of a submerged object utilizing acoustical wave energy.

One of the principal objects of this invention is to provide an underwater apparatus for inspecting submerged objects with acoustical wave energy at depths in the neighborhood of 500 meters.

A further object of this invention is to provide underwater apparatus for acoustically inspecting the interior of a submerged object at substantial depths in which a diver is provided with a visual display of acoustical information to assist the diver in his inspection.

These and other objects and advantages of this invention will become apparent upon reading the following detailed description of a preferred embodiment.

BRIEF DESCRIPTION OF THE DRAWINGS

The preferred embodiment of this invention is illustrated in the accompanying drawings, in which:

FIG. 2 is a pictorial and schematic block diagram of the electrical and electronic system for acoustically and visually inspecting the submerged object; and FIG. 3 is a pictorial view of a portable acoustical and optical probe that may be easily carried and manipulated by a diver to move the probe easily over a rather large object having a contoured surface.

FIG. 4 is a schematic block view of an electronic acoustical scan control system utilized for acoustically scanning the interior of the object as the probe is being moved over the object.

DETAILED DESCRIPTION OF A PREFERRED EMBODIMENT

Figure 1:
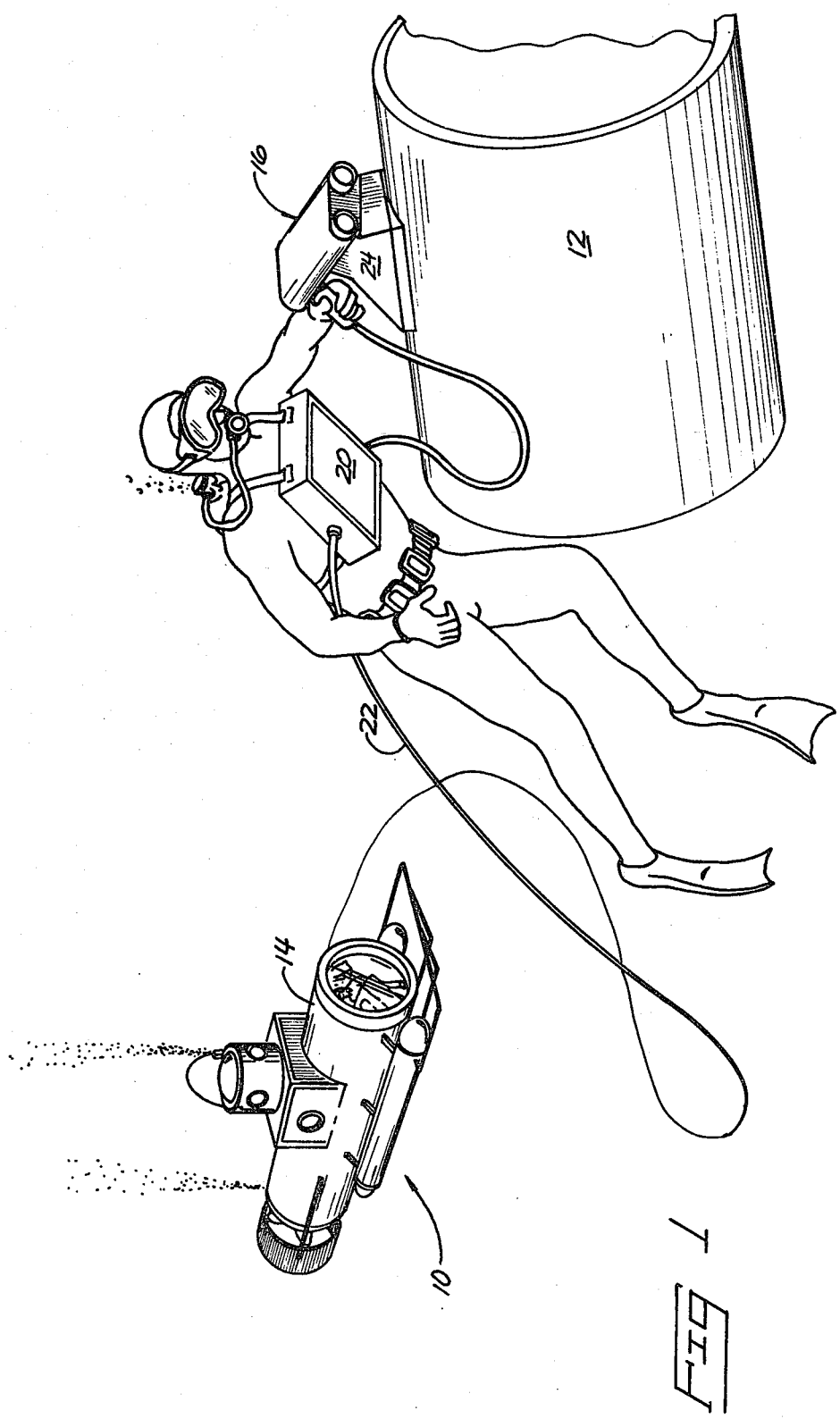
FIG. 1 is a pictorial view of an underwater apparatus encompassing the principal features of this invention for acoustically inspecting a submerged object such as the base of an offshore oil rig.

Referring now in detail to the drawings, there is illustrated in FIG. 1 an underwater apparatus 10 for nondestructively acoustically inspecting the interior of a submerged object 12. FIG. 1 illustrates the acoustical inspection of a segment of the base portion of an offshore oil rig. The underwater apparatus 10 is designed to operate at substantial depths of up to 500 meters below the ocean surface. The underwater apparatus 10 is capable of optically inspecting the surface of the submerged object 12 and acoustically inspecting the interior of the object to determine whether or not the object has any defects or flaws.

One of the principal components of the underwater apparatus is a pressurized underwater craft or vehicle 14 such as a submarine that is capable of transporting both humans and equipment to the submerged object.

Another principal component of the underwater apparatus 10 is a portable probe 16 that may be easily carried and manipulated by a diver 18 for directing acoustical wave energy into the volume of the submerged object 12 and visual inspecting the surface of the submerged object. The diver carries a diver electronic package 20 that is capable of withstanding substantial pressure for the operation of the portable probe 16.

The apparatus 10 includes an umbilical transmission cable 22 that extends from the submerged object 12 outward therefrom to the diver electronic package 20 to enable the diver to move over the submerged object 12 while the vehicle 14 remains in the vicinity.

The portable acoustical and optical probe 16 has a housing 24 that is of a size and shape to be easily moved by the diver over the surface of the submerged object 12. The probe 16 includes acoustical transducers 25 that are activated to transmit acoustical wave energy into the interior of the submerged object 12 and to receive reflected acoustical wave energy from the interior of the object and to generate electronic signals containing information with respect to the interior structure of the submerged object. In the described embodiment the acoustical transducers 25 are formed in a generally two dimensional array with acoustical transducers being mounted in a flexible backing material that is sufficiently flexible to accommodate a multitude of contours of the submerged object so as to easily arrange the array of acoustical transducers 25 in compliance with the contour of the submerged object to effectively transmit the acoustical energy into the object and to receive the reflected acoustical wave energy from the object.

The diver electronic pressurized package 20 (FIG. 2) includes transmit amplifiers 28 to amplify transmit signals to drive the acoustical transducers. Furthermore, the package includes receive amplifiers 30 that are operatively connected to the transducers for amplifying receive signals. Additionally the package 20 includes acoustical image electronics 32.

The probe 16 further includes an acoustical image display 34 (FIG. 3) at the rear of the probe and in the normal view of the diver so that the diver may obtain a visual image of the acoustical information. The display 34 assists the diver in his inspection particularly in locating flaws and in carefully inspecting the extent of the flaw or defect. In a preferred embodiment the acoustical image display 34 has a light emitting diode (LED) real time display of the acoustical information (interference patterns).

The optical inspection system includes a light 36 that is part of the probe 16 for directing optical radiation onto the surface of the submerged object to assist the diver in his inspection and to provide an optical record of the surface being internally inspected with the acoustical wave energy. The optical inspection system includes a vidicon camera 38 that is part of the probe 16 for providing a video record of the submerged object surface being inspected.

The acoustical inspection system further includes an electronic scan control means 42 that is mounted within the underwater vehicle 14 for controlling the energization of the acoustical transducers 25 to effectively sequentially scan the internal volume of submerged object during the inspection process. The scan control means 42 sequentially activates selected combinations of the transducers in selected phase relationships to sequentially scan the interior of the object with focused acoustical beams.

The electronic receive signals that are generated by the acoustical transducers 25 in a receive mode are processed by an image formation means 44 that is mounted within the vehicle 14 for visually displaying an acoustical image of the interior of the object on an acoustical image display means 46. Preferably the display means 46 is a cathode ray tube. The acoustical information from the acoustical transducers 25 may be displayed on the CRT unit utilizing the techniques described in the Becker et al U.S. Pat. No. 3,792,423 granted Feb. 12, 1974 and the Collins et al U.S. Pat. No. 4,021,771 granted May 3, 1977. Both of these patents are incorporated by reference as part of description as examples of visually displaying acoustical information received by acoustical scanning of the interior of an object. The information may be displayed in B-scan, C-scan or holographic scan form. An example of an electronic acoustical scan control means 42 utilizing an array 27 is illustrated in FIG. 4. The electronic scan control means 42 for sequentially scanning the volume includes a clock means 126 for generating clock pulses at regular intervals at a desired high frequency, such as 64 Mhz. The clock means 126 is operatively connected to a plurality of electronic frequency-divider means 128 that are associated with corresponding acoustical transducers 25. In a preferred embodiment, each electronic frequency divider 128 is associated with each transducer in a particular column. In some embodiments, it may be desirable to utilize a separate electronic-frequency divider 128 for each acoustical transducer 25. The electronic-divider means 128 receives the high frequency clock pulses from the clock means 126 and generates a low frequency transmit pulse signal that has a frequency that is a fraction of the clock pulse. In one embodiment, the frequency-divider means 128 generates a transmit pulse signal having a frequency that is 1/32 of the frequency of the clock pulses or 2 Mhz.

The electronic means 42 includes, in a preferred embodiment, a multiplexer 130 for sequencing the application of the transmit pulse signals sequentially to the transducers of the various rows. The transmit pulse signals are then applied to individual transmit amplifiers 132 for driving the transducers to generate and direct the acoustical wave energy into the volume.

When the transmitted acoustical wave energy impinges upon a discontinuity, reflected acoustical beams are generated that are reflected back to the acoustical transducers 25. The acoustical transducers 25 then produce received pulse signals in response to the reflected acoustical pulses. Because of the substantially larger magnitude of the transmit signal, isolation circuits 134 are utilized to discriminate and filter out the influence of transmit signal in the received circuitry. The received signals are processed through a demultiplexer 136 that is indexed complementary to a multiplexer 130 for sequencing the receive signals from row-to-row. The received signals passing from the demultiplexer 136 are amplified by receive amplifiers 138.

The electronic scan control means 42 includes a phase control means generally designated with the numeral 146 and a sequencing control means generally designated with the numeral 148 (FIG. 4).

The phase control means 146 preferably includes a plurality of erasable programmable read-only-memory (EPROM) means 150 that are associated with corresponding transducers and corresponding electronic frequency-divider means 128 for controlling and adjusting the phases of the transmit pulse signals in relation to the distances between the corresponding acoustical transducers and selected focal points. The objective is to have the acoustical wave energy generated by each selected combination of transducers to be in phase at the selected focal point. The focused acoustical energy concentrates acoustical energy at the focal point in order to obtain high contrast acoustical information. Additionally, the phase control means 146 includes a plurality of balanced mixer means 152 (associated with corresponding transducers) that are positioned in the received circuitry for mixing the phase adjusted transmit pulse signals with corresponding receive signals.

In response to the phase adjusted transmit pulse signals and received pulse signals, each balance mixer means 152 generates a resultant holographic signal containing holographic information from that portion of the volume identified with the selected focal point as received by a corresponding acoustical transducer 25. When the receive signal is in phase with the phase adjusted transmit signal, the resultant holographic signal has maximum amplitude. Consequently, the balance mixer means 152 serves to effectively focus the selected acoustical transducers in the receive mode to emphasize the reflected acoustical energy originating at the focal point or generated within the selected portion of the volume and to filter out or deemphasize reflected energy received from outside the selected portion. Stated another way, if the acoustical wave energy is reflection from the location of the focal point, a high amplitude holographic signal is generated which provides for high amplitude processing which in effect filters out acoustical wave energy received from portions of the volume outside the selected volume portion.

The resultant holographic signals are processed through low pass filters 154 to remove high frequency waves that may be carried on the signal.

The sequence control means 148 preferably includes a master read-only-memory (ROM) means 156 that is operatively connected to the transducers 25 for sequencing each combination of transducers in a programmed schedule to sequentially focus the beams at the desired focal points to three dimensionally scan a selected portion of the object 12. During the scanning sequence, the ROM 156 indexes the multiplexer 130 and the demultiplexer 136 from row to row. The ROM 156 also programs the EPROMS 150 to adjust the phases of the transmit signals in accordance to the distances from the corresponding acoustical transducers to the selected focal points. The EPROMS 150 in effect control and adjust the phases of the transmit signals generated by the frequency-divider means 128.

Additionally, the sequence control means 148 includes signal sampling means 158 that are associated with corresponding transducers 25 and balance mixers 152 for time sampling the resulting holographic acoustical signals from the balance mixers 152. The time sampling is controlled by the ROM 156 to time sample the signal at the probable time of maximum amplitude. The signal sampling means 158 produces a time sampled holographic signal from each transducer of the selected combination.

Such electronic means 42 includes summing means 160 for receiving the time sampled holographic signals from the sampling means 158 and forming a composite acoustical/holographic signal for each portion of the volume identified by selected coordinate focus point. The summing means 160 effectively sums the amplitude of the individual holographic signals from each selected transducer and provides for a composite signal. The composite acoustical/holographic signal is then presented to electronic squaring means 162 for squaring the composite signal to increase the sensitivity and contrast of the composite signal. A signal sampling means 166 is provided for sequentially sampling the individual squared, composite holographic signals to sequentially feed such signals to the image formation means 44.

The video or optical inspection system includes a power source 48 that is positioned in the vehicle 14 and is connected to the light 36 for activating the light. Additionally the optical inspection system includes an optical image display 50 in the vehicle 14 for visually displaying the optical information from the vidicon camera 38 to enable an observer in the vehicle 14 to monitor the inspection of the object. The operator within the underwater craft 14 may visually monitor both the acoustical image display 46 and the optical image display 50 and communicate with the diver 18 to facilitate the inspection process. The apparatus 10 further includes the data recording means 52 for recording both the optical and acoustical information received by the acoustical transducers 25 and the vidicon camera 38 so as to provide a permanent record of the inspection of the submerged object 12.

It should be understood that the above described embodiment is simply illustrative of the principals of this invention and that numerous other embodiments may be readily devised without deviating therefrom. Therefore, only the following claims are intended to define this invention.

What is claimed is:

1. Underwater apparatus for acoustically inspecting a volume of a submerged object, comprising:
   an underwater vehicle capable of transporting humans and equipment to a submerged object having an accessible surface;
   a portable acoustical probe capable of being carried and easily applied to the surface of the submerged object by a diver for acoustically inspecting the interior of the object;
   a data transmission and control cable of a desired length operatively interconnecting the portable acoustical probe with the underwater vehicle to enable the probe to be operated spaced from the underwater vehicle;
   said portable acoustical probe having a generally two dimensional array of acoustical transducers for receiving transmit electrical pulse signals and in response thereto directing pulsed acoustical wave energy into the volume during a transmit mode and for receiving reflected pulsed acoustical wave energy from the volume and in response thereto generating received electrical pulse signals during a receive mode;
   electronic scan control means operatively connected to the transducers (a) generating the transmit electrical pulse signals, (b) for selecting various combinations of the transducers with each combination of transducers associated with a portion of the volume having a selected focal point, (c) for adjusting the phases of the transmit electrical signals in relation to the relative distances between the selected transducers and the selected focal point during the transmit mode, (d) for mixing the phase adjusted transmit electrical pulse signals with the received pulse signals to focus the combination of the transducers on the corresponding selected focal point during the receive mode, and (e) for sequencing the combination of transducers during both the transmit and receive modes to sequentially scan portions of the interior to obtain high contrast acoustical information from such scanned portions;
   visual display means in the underwater vehicle operatively connected to the electronic control means and responsive to the electrical signals for displaying a real-time visual image of the interior of the object.

2. The underwater apparatus as defined in claim 1 wherein the electronic scan control means includes a plurality of programmable read-only-memory means for controlling the phases of the transmit electrical pulses.

3. The underwater apparatus as defined in claim 2 wherein at least one of the programmable read-only-memory means has erasable program capability.

4. The underwater apparatus as defined in claim 2 wherein the electronic scan control means includes a read-only-memory means operatively connected to the transducers for sequencing the combination of transducers to sequentially scan the volume portion by portion.

5. The underwater apparatus as defined in claim 1 wherein the portable probe includes a video camera for receiving an optical image of the exterior of the object and wherein the apparatus includes a cathode ray tube means operatively connected to the video camera for displaying a real time optical image of the exterior of the object.

6. The underwater apparatus as defined in claim 1 further comprising means for storing the electrical signals in the underwater vehicle.

7. The underwater apparatus as defined in claim 1 wherein the probe includes a second visual display means that is responsive to the electrical signals for displaying a real-time acoustical image of the interior of the object for the benefit of the diver.

* * * * *